US012594049B2

(12) United States Patent
    Tezuka et al.

(10) Patent No.: US 12,594,049 B2
(45) Date of Patent: Apr. 7, 2026

(54) RADIOGRAPHIC IMAGING APPARATUS AND CONTROL METHOD THEREOF

(71) Applicant: CANON KABUSHIKI KAISHA, Tokyo (JP)

(72) Inventors: Shimpei Tezuka, Tochigi (JP); Akiya Nakayama, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 235 days.

(21) Appl. No.: 18/501,465

(22) Filed: Nov. 3, 2023

(65) Prior Publication Data

US 2024/0148350 A1     May 9, 2024

(30) Foreign Application Priority Data

Nov. 7, 2022     (JP) ................................. 2022-178059

(51) Int. Cl.
    *A61B 6/00*        (2024.01)
    *A61B 6/42*        (2024.01)
    *A61B 6/58*        (2024.01)

(52) U.S. Cl.
    CPC ............ *A61B 6/541* (2013.01); *A61B 6/4208* (2013.01); *A61B 6/563* (2013.01); *A61B 6/566* (2013.01); *A61B 6/586* (2013.01)

(58) Field of Classification Search
    CPC ....... A61B 6/541; A61B 6/4208; A61B 6/563; A61B 6/566; A61B 6/586
    See application file for complete search history.

(56)                 References Cited

U.S. PATENT DOCUMENTS

2014/0254760 A1*   9/2014   Hiroike .................... A61B 6/54
                                                        378/62

FOREIGN PATENT DOCUMENTS

JP            6080421 B2     2/2017
JP         2021118797 A   *   8/2021   ............. G16H 30/20

* cited by examiner

*Primary Examiner* — Casey Bryant
(74) *Attorney, Agent, or Firm* — Canon U.S.A., Inc. IP Division

(57)                 ABSTRACT

A radiographic imaging apparatus configured to be able to communicate with a control apparatus includes: a radiation detecting unit configured to detect incident radiation rays to acquire a radiographic image; a storage unit configured to, in a case where radiographic imaging is performed when in a first imaging state, in which a state of communication with the control apparatus is abnormal, store radiographic imaging information from the radiographic imaging; and a communication control unit configured to, upon a transition from the first imaging state to a second imaging state, in which the state of communication with the control apparatus is normal, transmit the radiographic imaging information stored in the storage unit to the control apparatus.

10 Claims, 9 Drawing Sheets

RADIOGRAPHIC IMAGING APPARATUS AND CONTROL METHOD THEREOF

BACKGROUND OF THE DISCLOSURE

Field of the Disclosure

The present disclosure relates to a radiographic imaging apparatus and a control method thereof.

Description of the Related Art

In related art, the following radiographic imaging apparatuses and systems have been commercialized as products. Radiation rays are applied from a radiation generating apparatus to a subject. A radiographic image is acquired by digitizing the distribution of intensity of the radiation rays having passed through the subject. Image processing is performed on the acquired radiographic image, thereby obtaining a clear radiographic image.

Such a radiographic imaging apparatus is required to be capable of storing various kinds of information about radiographic imaging (radiographic imaging information) either in association with an acquired radiographic image or inclusive of the acquired radiographic image.

There exists a situation where a user wants to perform imaging on an emergency basis even though a radiographic imaging apparatus is in a state of being unable to communicate with a control apparatus due to occurrence of some kind of abnormal status in the control apparatus configured to control the radiographic imaging apparatus. For example, Japanese Patent No. 6,080,421 discloses a method for transition to a specific mode by not using a command communication line, via which a radiographic imaging apparatus is controlled, but using an image communication line so that operation in the specific mode can be performed in such an emergency-imaging situation.

However, in the emergency-imaging situation disclosed in Japanese Patent No. 6,080,421, since the control apparatus is in a state of being unable to communicate with the radiographic imaging apparatus due to occurrence of some kind of abnormal status, no record of radiographic imaging information about radiographic imaging (emergency imaging) is left, making it difficult to grasp what kind of radiographic imaging was executed.

SUMMARY OF THE DISCLOSURE

Addressing this issue, the present disclosure aims to provide a scheme that makes it possible to grasp what kind of radiographic imaging was executed in a case of execution of the radiographic imaging at a radiographic imaging apparatus while the state of communication with a control apparatus is abnormal.

A radiographic imaging apparatus according to a certain aspect of the present disclosure is a radiographic imaging apparatus configured to be able to communicate with a control apparatus, the radiographic imaging apparatus including: a radiation detecting unit configured to detect incident radiation rays to acquire a radiographic image; a storage unit configured to, in a case where radiographic imaging is performed when in a first imaging state, in which a state of communication with the control apparatus is not normal, store radiographic imaging information in the radiographic imaging; and a communication control unit configured to, upon a transition from the first imaging state to a second imaging state, in which the state of communication with the control apparatus is normal, transmit the radiographic imaging information stored in the storage unit to the control apparatus.

A radiographic imaging apparatus according to another aspect of the present disclosure is a radiographic imaging apparatus configured to be able to communicate with a control apparatus, the radiographic imaging apparatus including: a radiation detecting unit configured to detect incident radiation rays to acquire a radiographic image; an input unit configured to input examination information; an acquisition unit configured to acquire irradiation execution information in irradiation with the radiation rays executed at a radiation generating apparatus configured to generate the radiation rays; a storage unit configured to store radiographic imaging information that includes at least one of the examination information, image acquisition information in the radiographic image, and the irradiation execution information while radiographic imaging is being executed; and a communication control unit configured to transmit the radiographic imaging information stored in the storage unit to the control apparatus after execution of the radiographic imaging.

The present disclosure further includes a method of controlling the radiographic imaging apparatus stated above.

Further features of the present disclosure will become apparent from the following description of exemplary embodiments with reference to the attached drawings.

DESCRIPTION OF THE EMBODIMENTS

With reference to the drawings, modes (embodiments) for carrying out the present disclosure will now be described.

First Embodiment

First, a first embodiment of the present disclosure will now be described.

Figure 1:
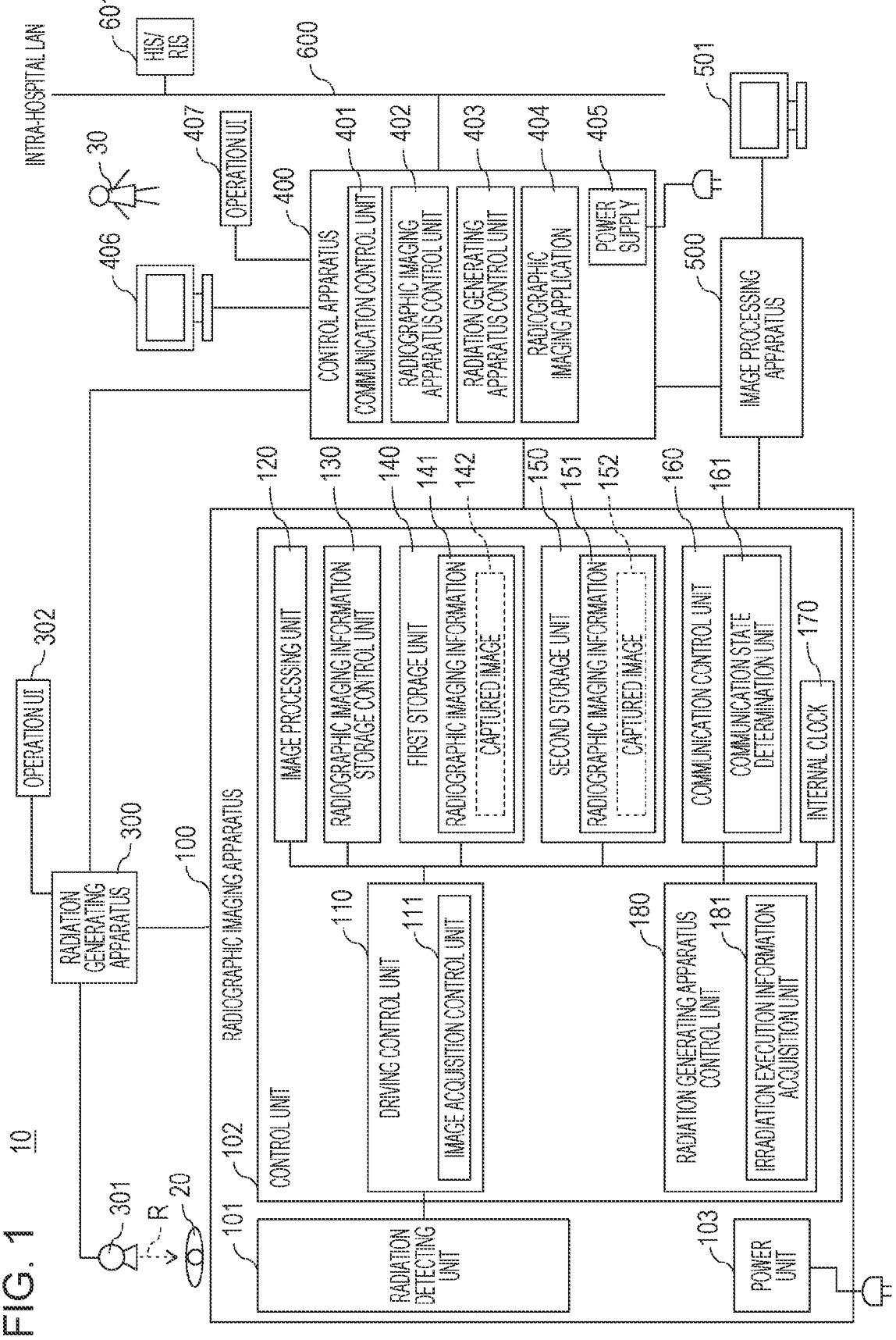
FIG. 1 is a diagram that illustrates an example of a schematic configuration of a radiographic imaging system according to a first embodiment of the present disclosure.

FIG. 1 is a diagram that illustrates an example of a schematic configuration of a radiographic imaging system 10 according to a first embodiment of the present disclosure. As illustrated in FIG. 1, the radiographic imaging system 10 includes a radiographic imaging apparatus 100, a radiation generating apparatus 300, a radiation source 301, an operation UI 302, a control apparatus 400, a display apparatus 406, an operation UI 407, an image processing apparatus 500, and a display apparatus 501. The radiographic imaging system 10 further includes, as illustrated in FIG. 1, an intra-hospital LAN 600 and an RIS (Radiology Information System) or HIS (Hospital Information System) 601.

Based on control by the control apparatus 400 and the radiographic imaging apparatus 100 (radiation generating apparatus control unit 180), the radiation generating apparatus 300 generates radiation rays R from the radiation source 301. Based on control by the radiation generating apparatus 300, the radiation source 301 emits the radiation rays R toward a subject 20 and the radiographic imaging apparatus 100 (radiation detecting unit 101) for irradiation therewith. The operation UI 302 is, for example, a user interface enabling an operator 30 of the radiographic imaging system 10 to operate the radiation generating apparatus 300. In the present embodiment, the operation UI 302 is used for setting irradiation conditions of the radiation rays R and giving irradiation instructions of the radiation rays R, etc. In the present embodiment, the radiation source 301 and the operation UI 302 can be configured as components included in the radiation generating apparatus 300.

The radiographic imaging apparatus 100 performs radiographic imaging of the subject 20. The radiographic imaging apparatus 100 is configured to be able to communicate with the radiation generating apparatus 300, the control apparatus 400, and the image processing apparatus 500. As illustrated in FIG. 1, the radiographic imaging apparatus 100 includes the radiation detecting unit 101, a control unit 102, and a power unit 103.

The radiation detecting unit 101 detects incident radiation rays R (inclusive of the radiation R rays having passed through the subject 20) to generate and acquire a radiographic image of the subject 20.

The control unit 102 controls the operation of the radiographic imaging apparatus 100 centrally and performs various kinds of processing. As illustrated in FIG. 1, the control unit 102 includes a driving control unit 110, an image processing unit 120, a radiographic imaging information storage control unit 130, a first storage unit 140, a second storage unit 150, a communication control unit 160, an internal clock 170, and the radiation generating apparatus control unit 180.

The driving control unit 110 controls the driving of the radiation detecting unit 101. The driving control unit 110 includes an image acquisition control unit 111 configured to perform control in acquiring, at the radiation detecting unit 101, a radiographic image that is acquired by irradiation with the radiation rays R and an offset image, etc. that is acquired without irradiation with the radiation rays R.

The image processing unit 120 performs image processing such as offset correction, gain correction, and missing-pixel compensation on images acquired from the radiation detecting unit 101 via the driving control unit 110.

The radiographic imaging information storage control unit 130 performs control for storing radiographic imaging information in radiographic imaging of the subject 20.

The first storage unit 140 is, for example, a volatile memory and stores radiographic imaging information 141 (which can include a captured image 142 of the subject 20) and the like. The first storage unit 140 may store the captured image 142 in association with the radiographic imaging information 141.

The second storage unit 150 is, for example, a non-volatile memory and stores yet-to-be-transferred radiographic imaging information 151 (which can include a captured image 152 of the subject 20) and the like. The second storage unit 150 may store the captured image 152 in association with the radiographic imaging information 151. The second storage unit 150 stores various kinds of information and programs, etc. that are needed for the control unit 102 to perform various kinds of control and processing, and can store various kinds of information, etc. obtained by performing various kinds of control and processing by the control unit 102.

For example, the control unit 102 reads out the programs, etc. stored in the second storage unit 150 and, based on the read programs, performs overall control on the radiographic imaging apparatus 100. Alternatively, the control unit 102 may perform overall control on the radiographic imaging apparatus 100 by means of a control circuit such as an ASIC or perform overall control on the radiographic imaging apparatus 100 by means of both the programs and the control circuit.

The communication control unit 160 controls communication with the control apparatus 400, communication with the radiation generating apparatus 300, and communication with the image processing apparatus 500. The communication control unit 160 includes a communication state determination unit 161 configured to determine a state of communication with the control apparatus 400.

The internal clock 170 is a clock for acquiring captured time, elapsed time, and the like.

Based on an irradiation signal of the radiation rays R of the radiation generating apparatus 300, the radiation generating apparatus control unit 180 controls the irradiation timing of the radiation rays R. The radiation generating apparatus control unit 180 includes an irradiation execution information acquisition unit 181 configured to acquire irradiation execution information in irradiation with the radiation rays R executed at the radiation generating apparatus 300 configured to generate the radiation rays R. The irradiation execution information includes at least one of irradiation condition information of the radiation rays R and cumulative irradiation dose information of the radiation rays R. Information can be exchanged between the radiographic imaging apparatus 100 and the radiation generating apparatus 300 via a dedicated signal line. Moreover, exchanging of sync signals such as notification of a start and an end of irradiation with the radiation rays R and notification of an irradiation-possible timing of the radiation rays R, etc. is performed.

The power unit 103 supplies power to the radiation detecting unit 101 and the control unit 102, etc.

The control apparatus 400 controls the operation of the radiographic imaging system 10 centrally and performs various kinds of processing. As illustrated in FIG. 1, the control apparatus 400 includes a communication control unit 401, a radiographic imaging apparatus control unit 402, a radiation generating apparatus control unit 403, a radiographic imaging application 404, and a power supply 405.

The communication control unit 401 controls communication with the radiographic imaging apparatus 100, communication with the radiation generating apparatus 300, and communication with the intra-hospital LAN 600. The radiographic imaging apparatus control unit 402 controls the radiographic imaging apparatus 100, for example, controls conditions for image acquisition by the radiographic imaging apparatus 100. The radiation generating apparatus control unit 403 controls the radiation generating apparatus 300, for example, controls conditions for irradiation with the radiation rays R by the radiation generating apparatus 300. The radiographic imaging application 404 controls the radiographic imaging apparatus 100 and the radiation generating apparatus 300 and performs processing such as receiving an imaging order, registering examination information, gathering captured images from the radiographic imaging apparatus 100 and displaying the captured images, storing the capture-executed radiographic imaging information, and the like. The power supply 405 supplies power to each component of the control apparatus 400.

Based on control by the control apparatus 400, the display apparatus 406 displays various images and various kinds of information. For example, the display apparatus 406 displays a captured image that is a radiographic image having been captured, radiographic imaging information (a captured image may be included as a part of radiographic imaging information), and the like. The operation UI 407 is, for example, a user interface enabling the operator 30 of the radiographic imaging system 10 to operate the control apparatus 400 (for example, the radiographic imaging application 404). The operation UI 407 can be made up of, for example, a keyboard, a mouse, and the like. In the present embodiment, the display apparatus 406 and the operation UI 407 can be configured as components included in the control apparatus 400.

Communication between the control apparatus 400 and the radiographic imaging apparatus 100 and communication between the control apparatus 400 and the radiation generating apparatus 300 can be configured as follows. Specifically, information can be communicated by means of any one or more of cable-connected communication compliant with an RS232C standard, a USB standard, an Ethernet standard, a CAN standard, or the like, communication via a dedicated signal line, and wireless communication. Between the control apparatus 400 and the radiographic imaging apparatus 100, for example, communication for image data and control communication for setting image acquisition conditions and acquiring apparatus status and the like are performed. The image acquisition conditions herein include image size of a radiographic image (captured image) to be acquired, a frame rate at the time of moving-picture imaging, sensitivity conditions thereof, and the like. Between the control apparatus 400 and the radiation generating apparatus 300, control communication for, for example, setting radiographic irradiation conditions, acquiring apparatus status, communicating actual irradiation execution information, and the like are performed.

After performing image processing on a captured image outputted from the radiographic imaging apparatus 100, the image processing apparatus 500 outputs the processed image to the control apparatus 400. When in a state in which it is impossible to communicate with the control apparatus 400, captured images and the like outputted from the radiographic imaging apparatus 100 are outputted to the display apparatus 501 capable of performing display without going through the control apparatus 400.

The intra-hospital LAN 600 is a local area network installed in a hospital. The control apparatus 400 and the HIS/RIS 601 are connected to the intra-hospital LAN 600. The control apparatus 400 and the HIS/RIS 601 are capable of communicating with each other. For example, the control apparatus 400 and the HIS/RIS 601 can communicate an order for capturing a radiographic image, examination information including subject information about the subject 20 (in a case where the subject 20 is a patient, patient information), a captured image, radiographic imaging information, and the like.

Figure 2:
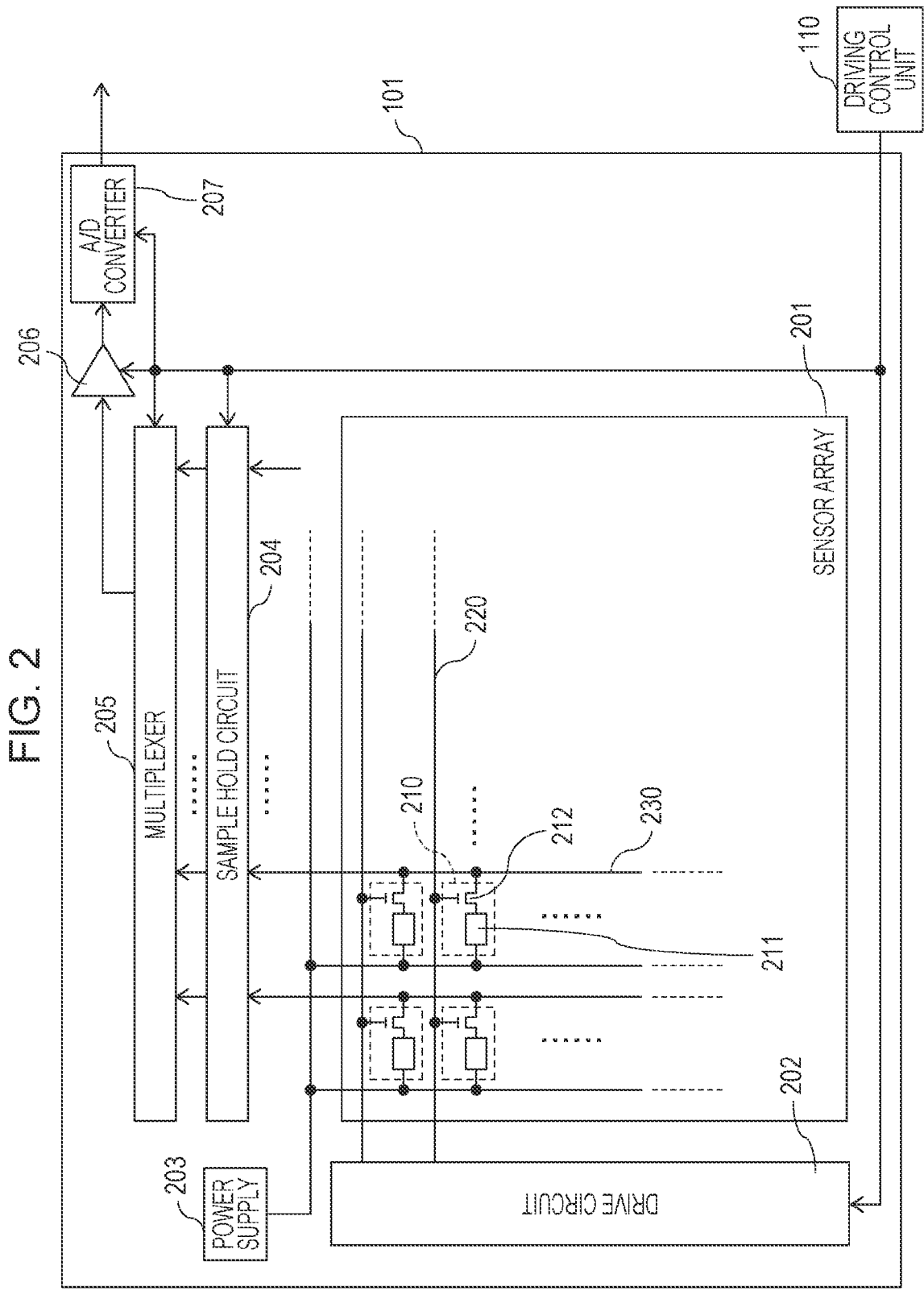
FIG. 2 is a diagram that illustrates an example of a schematic configuration of a radiation detecting unit illustrated in FIG. 1.

FIG. 2 is a diagram that illustrates an example of a schematic configuration of the radiation detecting unit 101 illustrated in FIG. 1. In FIG. 2, the same reference numerals are assigned to components that are the same as those illustrated in FIG. 1, and a detailed explanation thereof will be omitted.

As illustrated in FIG. 2, the radiation detecting unit 101 includes a sensor array 201, a drive circuit 202, a power supply 203, a sample hold circuit 204, a multiplexer 205, an amplifier 206, and an A/D converter 207.

The sensor array 201 includes a plurality of pixels 210 arranged in a two-dimensional array layout made up of a plurality of rows and a plurality of columns. Power is supplied to each of the pixels 210 from the power supply 203. Each of the pixels 210 includes a conversion element 211 and a switch element 212 such as a TFT. In the present embodiment, the conversion element 211 can be formed of a phosphor layer (scintillator layer) and a photoelectric conversion element. In the present embodiment, a phosphor layer configured to convert incident radiation rays R into light such as visible light is formed on each of the pixels 210, and the photoelectric conversion element converts the light generated at the phosphor layer into charge that is an electric signal. Although the phosphor layer (scintillator layer) and the photoelectric conversion element make up the conversion element 211 in the present embodiment, for example, the conversion element 211 may be configured as a so-called direct-conversion-type conversion element that converts incident radiation rays R into charge directly, without providing any phosphor layer. Moreover, in the present embodiment, it is possible to perform charge accumulation and charge readout by switching the switch element 212 of each of the pixels 210 between ON and OFF, thereby acquiring a radiographic image.

For the pixels 210 of each row of the sensor array 201, an ON voltage for switching the switch elements 212 is applied to a drive line 220 by the drive circuit 202, and, upon this voltage application, the switch elements 212 of the pixels 210 of each row turn ON. By this means, charge generated at the conversion elements 211 of the pixels 210 including the switch elements 212 that are ON is held at the sample hold circuit 204 via each of signal lines 230. After that, electric signals based on the pixel-output charge held at the sample hold circuit 204 are read out one after another via the multiplexer 205, are amplified by the amplifier 206, and are thereafter converted into digital radiographic image data by the A/D converter 207.

The pixels 210 of the row for which charge readout has finished are returned to a charge accumulation state by applying an OFF voltage for switching the switch elements 212 to the drive line 220 by the drive circuit 202.

As described above, the drive circuit 202 drives the pixels 210 of the rows of the sensor array 201 sequentially, and, finally, electric signals based on the output charge of all of the pixels 210 are converted into digital values. By this means, it is possible to read out radiographic image data. The controlling of the driving of these components of the radiation detecting unit 101, the controlling of readout operation, and the like are performed by the driving control unit 110. The digital-converted radiographic image data is stored as the captured image 142 into the first storage unit 140 illustrated in FIG. 1. It is possible to perform radiographic imaging to capture a moving picture by performing this operation successively. It is also possible to store, into the first storage unit 140 as an offset image, image data having been read out in a state of non-irradiation with the radiation rays R while performing the same driving as in acquiring a radiographic image.

The acquired radiographic image can be transferred to the image processing apparatus 500 via the communication control unit 160 after having been subjected to processing such as offset correction, gain correction, and missing-pixel compensation by the image processing unit 120. The execution of these kinds of correction processing is not limited to execution at the radiographic imaging apparatus 100. For example, the acquired radiographic image and the acquired offset image may be transferred to the image processing apparatus 500 without correction, and the correction processing may be performed inside the image processing apparatus 500.

The radiographic imaging apparatus 100 according to the present embodiment, as its imaging state in radiographic imaging of the subject 20, has a normal imaging state, in which it is possible to perform radiographic imaging while performing communication with the control apparatus 400, and an emergency imaging state, in which radiographic imaging is performed even though communication with the control apparatus 400 cannot be performed for some reason or other.

Figure 3:
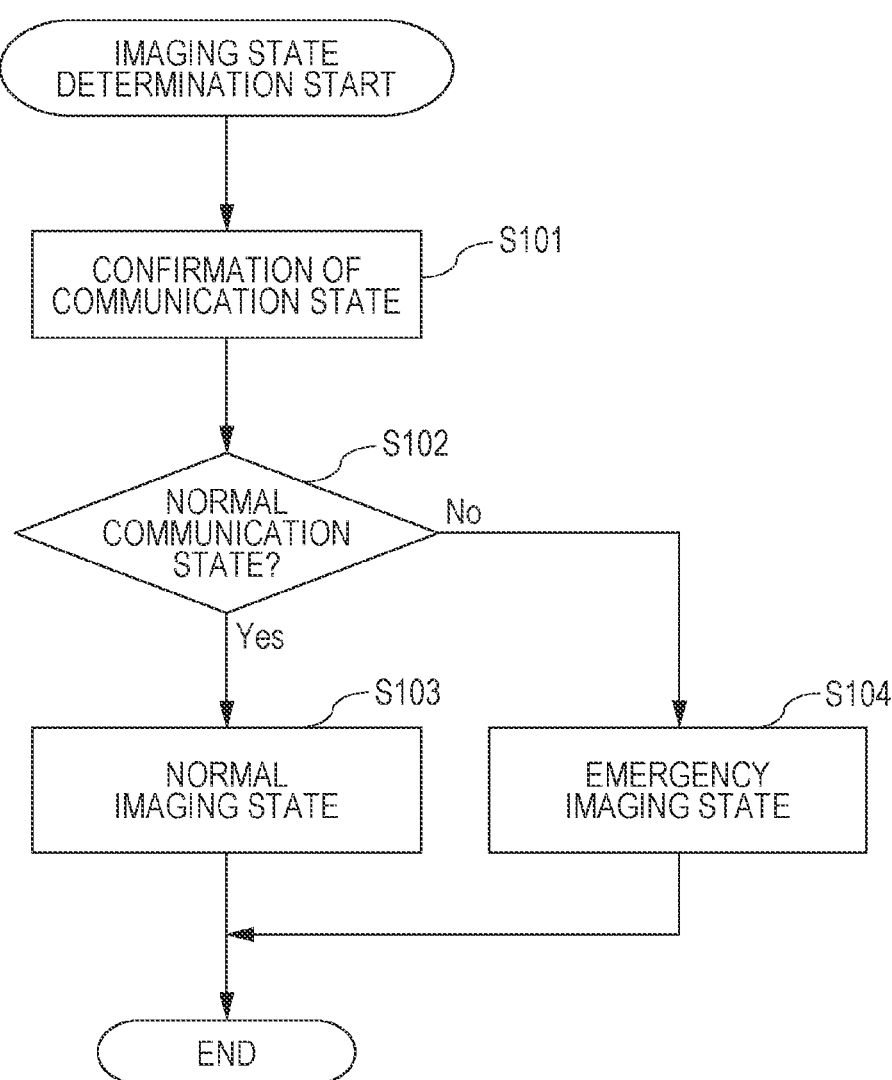
FIG. 3 is a flowchart that illustrates an example of processing steps in a method of imaging state determination performed by a radiographic imaging apparatus according to the first embodiment of the present disclosure.

FIG. 3 is a flowchart that illustrates an example of processing steps in a method of imaging state determination performed by the radiographic imaging apparatus 100 according to the first embodiment of the present disclosure.

First, in step S101, the communication state determination unit 161 confirms a state of communication with the control apparatus 400. Confirming a state of communication in step S101 is, for example, performed as follows. The control apparatus 400 transmits a command for confirming a communication state periodically to the radiographic imaging apparatus 100 (for example, the communication control unit 160). Upon receiving the command from the control apparatus 400, the radiographic imaging apparatus 100 (for example, the communication control unit 160) returns an acknowledgment command to the control apparatus 400. Then, in a case where the command is received from the control apparatus 400 periodically, the communication state determination unit 161 determines that the state of communication with the control apparatus 400 is normal. If no command is received from the control apparatus 400 for a certain period, the communication state determination unit 161 determines that the state of communication with the control apparatus 400 is not normal (abnormal).

Next, in step S102, the communication state determination unit 161 determines whether the state of communication with the control apparatus 400 confirmed in step S101 is normal or not.

If the result of determination in step S102 is that the state of communication with the control apparatus 400 confirmed in step S101 is normal (S102/Yes), the process proceeds to a step S103.

In step S103, for example, as an imaging state in radiographic imaging of the subject 20, the communication control unit 160 sets a normal imaging state, in which it is possible to perform radiographic imaging while performing communication with the control apparatus 400.

If the result of determination in step S102 is that the state of communication with the control apparatus 400 confirmed in step S101 is not normal (S102/No), the process proceeds to a step S104.

In step S104, for example, as an imaging state in radiographic imaging of the subject 20, the communication control unit 160 sets an emergency imaging state, in which radiographic imaging is performed even though communication with the control apparatus 400 cannot be performed for some reason or other.

The processing of the flowchart illustrated in FIG. 3 ends when the processing of the step S103 ends or when the processing of the step S104 ends.

In the normal imaging state illustrated in step S103 of FIG. 3, the image acquisition conditions for acquiring a radiographic image are set from the control apparatus 400. However, in the emergency imaging state illustrated in step S104 of FIG. 3, the image acquisition conditions are not set from the control apparatus 400 because it is impossible to communicate with the control apparatus 400. Therefore, in a case of the emergency imaging state illustrated in step S104 of FIG. 3, for example, operation is performed under the settings of specific image acquisition conditions (image size, frame rate, sensitivity, and the like) having been set in advance.

In the present embodiment, the emergency imaging state set in step S104 of FIG. 3 corresponds to "a first imaging state" of the case where the state of communication with the control apparatus 400 is not normal. In the present embodiment, the normal imaging state set in step S103 of FIG. 3 corresponds to "a second imaging state" of the case where the state of communication with the control apparatus 400 is normal.

The radiographic imaging apparatus 100 according to the present embodiment stores, into the storage unit, radiographic imaging information (which can include a captured image that is a radiographic image having been captured) in radiographic imaging in a case where the radiographic imaging is performed when in the emergency imaging state set in step S104 of FIG. 3. The radiographic imaging information stored in the storage unit is transmitted to the control apparatus 400 when a transition from the emergency imaging state to the normal imaging state, in which the state of communication between the radiographic imaging apparatus 100 and the control apparatus 400 is normal, occurs due to a recovery of the control apparatus 400.

In the present embodiment, the radiographic imaging information includes at least one of examination information, image acquisition information, and irradiation execution information. The examination information includes at least one of a patient ID, which corresponds to subject information in radiographic imaging, and imaging protocol information. The image acquisition information includes at least one of a captured image that is a radiographic image acquired through radiographic imaging, date-and-time information of radiographic imaging, image acquisition conditions such as the number of frames in acquiring a radiographic image, and cumulative pixel value information in a region of interest at the radiation detecting unit 101. For example, the cumulative pixel value information is cumulative pixel value information in a region of interest in a moving picture that is a series of radiographic images acquired through radiographic imaging. The irradiation execution information includes at least one of information about irradiation conditions (tube voltage, tube current, irradiation time, and the like) of the radiation rays R by the radiation generating apparatus 300 and information about cumulative irradiation dose of the radiation rays R in capturing a series of moving images. The irradiation execution information that can be included in the radiographic imaging information may be irradiation execution information acquired by the irradiation execution information acquisition unit 181.

Figure 4:
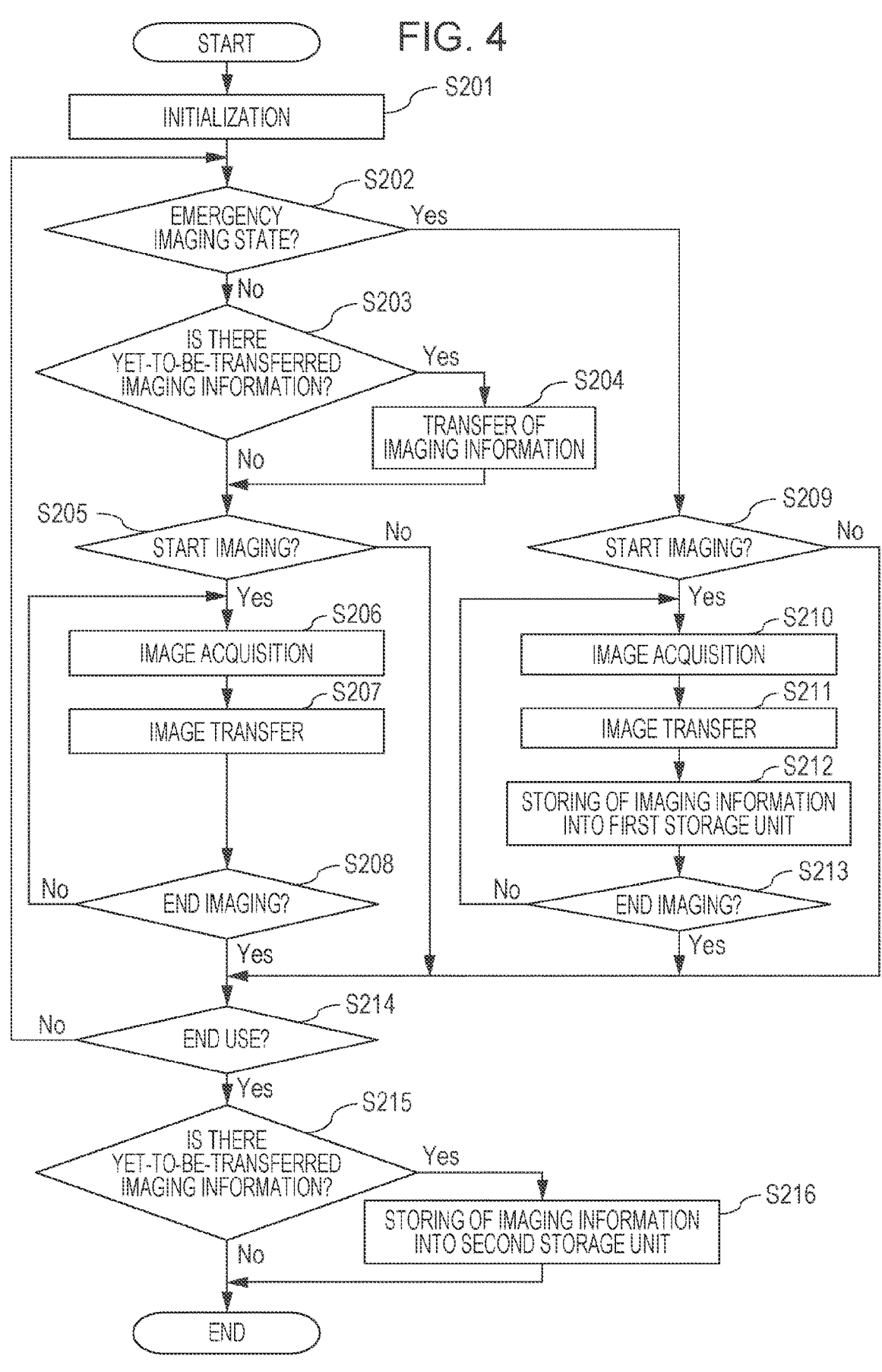
FIG. 4 is a flowchart that illustrates an example of processing steps in a control method of the radiographic imaging apparatus according to the first embodiment of the present disclosure.

FIG. 4 is a flowchart that illustrates an example of processing steps in a control method of the radiographic imaging apparatus 100 according to the first embodiment of the present disclosure.

First, when power supply from the power unit 103 starts upon the start of use of the radiographic imaging apparatus 100, in step S201, for example, the driving control unit 110 performs initializing processing such as imaging preparation operation, preparation of correction data such as offset correction data, and the like.

Next, in step S202, the communication control unit 160 determines whether or not the emergency imaging state is set as an imaging state in radiographic imaging of the subject 20.

If the result of determination in step S202 is that the emergency imaging state is not set as the imaging state in radiographic imaging of the subject 20 (if the normal imaging state is set) (S202/No), the process proceeds to a step S203.

In step S203, the radiographic imaging information storage control unit 130 determines whether or not there is yet-to-be-transferred radiographic imaging information 151 in the second storage unit 150, which is a non-volatile memory.

If the result of determination in step S203 is that there is yet-to-be-transferred radiographic imaging information 151 in the second storage unit 150 (S203/Yes), the process proceeds to a step S204.

In step S204, the communication control unit 160 transmits the yet-to-be-transferred radiographic imaging information 151 to the control apparatus 400.

When the processing of step S204 ends or when it is determined in step S203 that there is no yet-to-be-transferred radiographic imaging information 151 in the second storage unit 150 (S203/No), the process proceeds to a step S205.

In step S205, for example, based on whether or not there is an imaging start request from the radiation generating apparatus 300, the radiation generating apparatus control unit 180 determines whether or not to start radiographic imaging.

If the result of determination in step S205 is that radiographic imaging is started (S205/Yes), the process proceeds to a step S206.

In step S206, the driving control unit 110 starts imaging operation by the radiation detecting unit 101 to acquire a radiographic image.

Next, in step S207, the communication control unit 160 transfers the radiographic image acquired in step S206 to the image processing apparatus 500.

Next, in step S208, for example, based on whether or not there is an imaging stop request from the radiation generating apparatus 300, the radiation generating apparatus control unit 180 determines whether or not to end radiographic imaging. If the result of this determination is that radiographic imaging is not ended (S208/No), the process returns to the step S206, and processing for image acquisition (S206) and image transfer (S207) of the next frame is performed. Moving-picture imaging operation is performed by repeating these steps.

If the result of determination in step S208 is that radiographic imaging is ended (S208/Yes), or if it is determined in step S205 that radiographic imaging is not started (S205/No), the process proceeds to a step S214.

If the result of determination in step S202 is that the emergency imaging state is set as the imaging state in radiographic imaging of the subject 20 (S202/Yes), the process proceeds to a step S209.

In step S209, for example, based on whether or not there is an imaging start request from the radiation generating apparatus 300, the radiation generating apparatus control unit 180 determines whether or not to start radiographic imaging.

If the result of determination in step S209 is that radiographic imaging is started (S209/Yes), the process proceeds to a step S210.

In step S210, the driving control unit 110 starts imaging operation by the radiation detecting unit 101 to acquire a radiographic image.

Next, in step S211, the communication control unit 160 transfers the radiographic image acquired in step S210 to the image processing apparatus 500.

Next, in step S212, since the emergency imaging state is set, the radiographic imaging information storage control unit 130 stores information about the executed radiographic imaging into the first storage unit 140 as the radiographic imaging information 141. When this is performed, in the present embodiment, the radiographic image acquired in step S210 can be included as the captured image 142 in the radiographic imaging information 141.

Next, in step S213, for example, based on whether or not there is an imaging stop request from the radiation generating apparatus 300, the radiation generating apparatus control unit 180 determines whether or not to end radiographic imaging. If the result of this determination is that radiographic imaging is not ended (S213/No), the process returns to the step S210, and processing for image acquisition (S210) and image transfer (S211) of the next frame is performed. Moving-picture imaging operation is performed by repeating these steps.

If the result of determination in step S213 is that radiographic imaging is ended (S213/Yes), or if it is determined in step S209 that radiographic imaging is not started (S209/No), the process proceeds to the step S214.

In step S214, for example, based on whether or not there is a request from the control apparatus 400 for ending the use of the radiographic imaging apparatus 100, the communication control unit 160 determines whether or not to end the use of the radiographic imaging apparatus 100. If the result of this determination is that the use of the radiographic imaging apparatus 100 is not ended (S214/No), the process returns to the step S202, and the monitoring of the imaging state, the imaging start request, and the use end request of the radiographic imaging apparatus 100 is repeated.

If the result of determination in step S214 is that the use of the radiographic imaging apparatus 100 is ended (S214/Yes), the process proceeds to a step S215.

In step S215, the radiographic imaging information storage control unit 130 determines whether or not there is radiographic imaging information 141 that has not been transferred to the control apparatus 400 yet in the first storage unit 140, which is a volatile memory.

If the result of determination in step S215 is that there is radiographic imaging information 141 that has not been transferred to the control apparatus 400 yet in the first storage unit 140 (S215/Yes), the process proceeds to a step S216.

In step S216, the radiographic imaging information storage control unit 130 stores the radiographic imaging information 141 that has not been transferred to the control apparatus 400 yet and is stored in the first storage unit 140 into the second storage unit 150, which is a non-volatile memory, as the radiographic imaging information 151.

When the processing of the step S216 ends or when it is determined in step S215 that there is no radiographic imaging information 141 that has not been transferred to the control apparatus 400 yet in the first storage unit 140 (S215/No), the power supply from the power unit 103 is stopped. This terminates the processing of the flowchart illustrated in FIG. 4.

In the example illustrated in FIG. 4, in a case where the use of the radiographic imaging apparatus 100 is ended (S214/Yes), the radiographic imaging information that has not been transferred to the control apparatus 400 yet is stored into the second storage unit 150, which is a non-volatile memory. However, the scope of the present embodiment is not limited to this example. For example, said information may be stored into the second storage unit 150 as the radiographic imaging information 151 each time an image is acquired or may be stored into the second storage unit 150 as the radiographic imaging information 151 when the radiographic imaging stops.

Radiographic images of all frames acquired when in the emergency imaging state may be included in the radiographic imaging information 151 (or the radiographic imaging information 141) as the captured image 152 (or the captured image 142).

In a case where radiographic imaging of the subject 20 is performed for a long time, it is sometimes difficult to store radiographic images of all frames, for example, depending on the memory capacity of the first storage unit 140.

Storing radiographic images of all frames is not indispensable because the captured images that are stored are just for association for the purpose of management of the radiographic imaging information. In this case, the radiographic imaging information storage control unit 130 may select radiographic images of representative frames from among radiographic images of a plurality of frames acquired as a series of moving images when in the emergency imaging state and may include the selected images as the captured image 152 (or the captured image 142). The radiographic image of the representative frame that is selected may be the radiographic image acquired last in the series of moving images (the radiographic image of the last frame), and a configuration of using this last one as "last image hold" can be adopted. The radiographic images of the representative frames that are selected may be radiographic images of intermediate frames among the series of moving images.

As another example, radiographic images selected by sampling only frames of a preset designated cycle may be included as the captured image 152 (or the captured image 142). As another example, all of radiographic images of a pre-designated number of latest frames may be included as the captured image 152 (or the captured image 142), radiographic images of representative frames only may be included for those anteceding these latest frames, and radiographic images of the other frames may be discarded. As another example, images obtained by size-reducing or compressing radiographic images acquired when in the emergency imaging state may be included as the captured image 152 (or the captured image 142).

Figure 5:
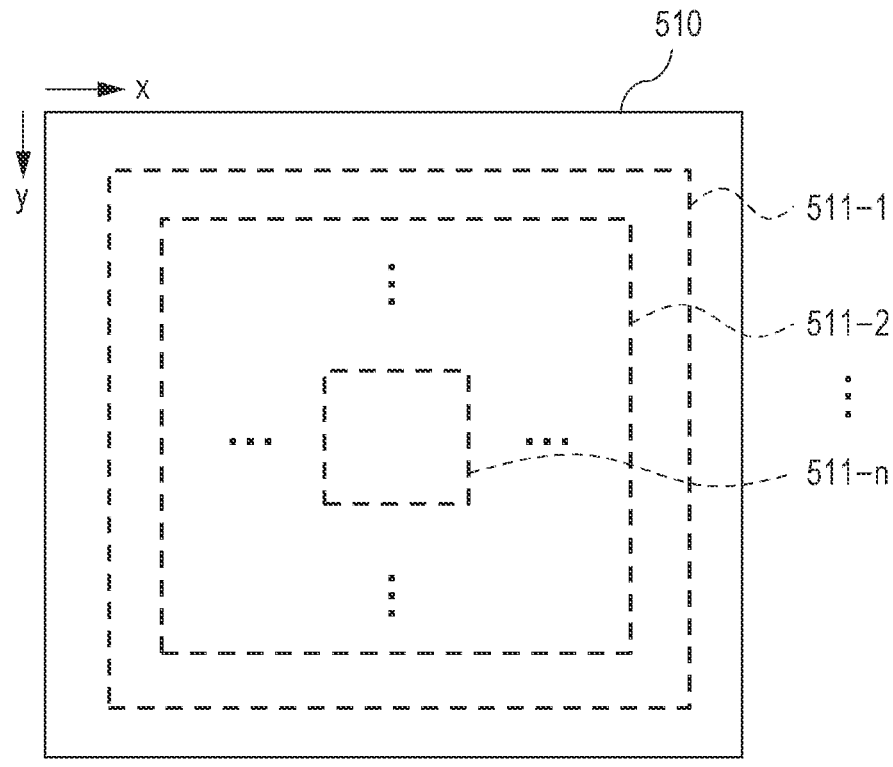
FIG. 5 is a diagram for illustrating the first embodiment of the present disclosure and explaining cumulative pixel value information in a region of interest that can be included as image acquisition information of radiographic imaging information.

FIG. 5 is a diagram for illustrating the first embodiment of the present disclosure and explaining cumulative pixel value information in a region of interest that can be included as image acquisition information of radiographic imaging information.

A region of interest 511 is preset in an image region 510 illustrated in FIG. 5. For example, in a case where a region of interest N (ROI_N) 511-*n* illustrated in FIG. 5 is set, a pixel average value of the region of interest N (ROI_N) 511-*n* is calculated. Then, pixel average values in the region of interest 511 of radiographic images of frames acquired in a series of moving images are summed, and the sum is stored into radiographic imaging information in association with the captured image as the cumulative pixel value information.

In a case where there is a collimator for adjusting an irradiation region to the radiation generating apparatus 300, the irradiation region is narrowed to a region that is narrower than the set region of interest 511. In this case, the radiation rays R impinge on only a part of the inside of the region of interest 511 and, therefore, there is a possibility that accurate cumulative pixel value information cannot be acquired. Therefore, when in the emergency imaging state, the radiation generating apparatus 300 may impose a limitation so that an irradiation region that is narrower than the set region of interest 511 cannot be set or impose a limitation so that a change cannot be made from a given irradiation region. As illustrated in FIG. 5, cumulative pixel value information may be stored for each of a plurality of region-of-interest patterns (a region of interest 1 (ROL_1) 511-1 to a region of interest N (ROI_N) 511-*n*) in the image region 510 of the radiographic imaging apparatus 100. In this case, after the recovery of the control apparatus 400, the radiographic imaging apparatus 100 can acquire, from the radiation generating apparatus 300, after transmitting radiographic imaging information to the control apparatus 400, history information of the irradiation region that was set when the control apparatus 400 was in emergency status. Then, the radiographic imaging apparatus 100 may select the cumulative pixel value information of the region-of-interest pattern that matches with the irradiation region that was set, and may include it in the radiographic imaging information.

Figure 6:
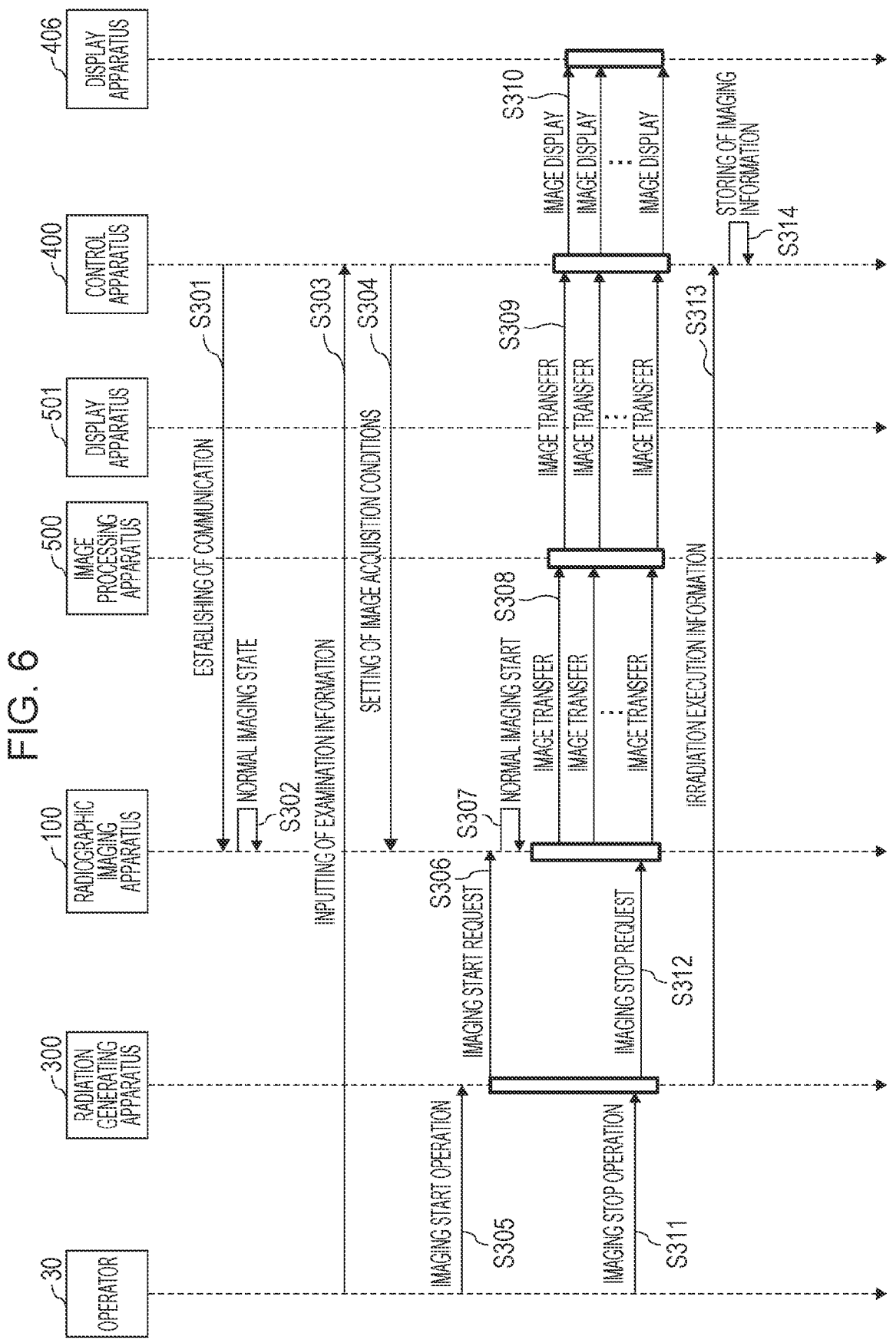
FIG. 6 is a sequence chart that illustrates an example of processing steps in a normal imaging state of the radiographic imaging system according to the first embodiment of the present disclosure.

FIG. 6 is a sequence chart that illustrates an example of processing steps in a normal imaging state of the radiographic imaging system 10 according to the first embodiment of the present disclosure. In FIG. 6, the same reference numerals are assigned to components that are the same as those illustrated in FIG. 1, and a detailed explanation thereof will be omitted.

After power activation of the radiographic imaging system 10, in step S301, a communication from the control apparatus 400 to the radiographic imaging apparatus 100 is established.

Next, in step S302, the radiographic imaging apparatus 100 is put into a normal imaging state by imaging state determination.

Next, in step S303, the operator 30 inputs examination information by using the operation UI 407 and the radiographic imaging application 404 of the control apparatus 400. The examination information includes, for example, a patient ID, an imaging protocol, and the like. The inputting of the examination information may be executed by receiving an imaging order from the HIS/RIS 601 connected to the intra-hospital LAN 600.

Next, in step S304, the control apparatus 400 sets image acquisition conditions corresponding to the imaging protocol included in the examination information to the radiographic imaging apparatus 100. By this means, when in the normal imaging state, the communication control unit 160 of the radiographic imaging apparatus 100 receives, from the control apparatus 400, image acquisition conditions for acquiring radiographic images.

Next, in step S305, the operator 30 performs an operation for starting imaging by using the operation UI 302 of the radiation generating apparatus 300 when performing radiographic imaging. This operation is performed by, for example, pushing an image request switch or a pedal of the operation UI 302.

Next, in step S306, a signal for an imaging start request is transmitted from the radiation generating apparatus 300 to the radiographic imaging apparatus 100.

Next, in step S307, upon receiving the imaging start request, the radiographic imaging apparatus 100 starts normal imaging operation corresponding to the set image acquisition conditions.

Next, in step S308, the radiographic imaging apparatus 100 transfers, to the image processing apparatus 500, a radiographic image acquired in accordance with the radiation rays R applied from the radiation generating apparatus 300.

Next, in step S309, the image processing apparatus 500 transfers a processed image to the control apparatus 400 after performing image processing as needed on the radiographic image received from the radiographic imaging apparatus 100.

Next, in step S310, the control apparatus 400 causes the display apparatus 406 to perform display after affixing necessary accompanying information (for example, examination information, date-and-time information, and the like) to the radiographic image received from the image processing apparatus 500.

In a case of moving-picture imaging, the processing from the image transfer in step S308 to the image display in step S310 is executed repeatedly.

After that, when stopping the radiographic imaging, in step S311, the operator 30 performs an operation for stopping the imaging by using the operation UI 302 of the radiation generating apparatus 300. This operation is performed by, for example, releasing the image request switch or the pedal of the operation UI 302 that has been being pushed.

Next, in step S312, a signal for an imaging stop request is transmitted from the radiation generating apparatus 300 to the radiographic imaging apparatus 100. Upon receiving the imaging stop request, the radiographic imaging apparatus 100 stops the radiographic imaging operation.

Next, in step S313, irradiation execution information such as information about the irradiation conditions (tube voltage, tube current, irradiation time, and the like) of the radiation rays R in the moving-picture imaging executed this time and cumulative dose information and the like is transmitted from the radiation generating apparatus 300 to the control apparatus 400.

Next, in step S314, the control apparatus 400 stores the acquired radiographic images, the examination information, and the irradiation execution information in association with one another as the radiographic imaging information. The radiographic imaging information may be transferred to an external server via the intra-hospital LAN 600 and may be stored thereat, as the case may be.

Figure 7:
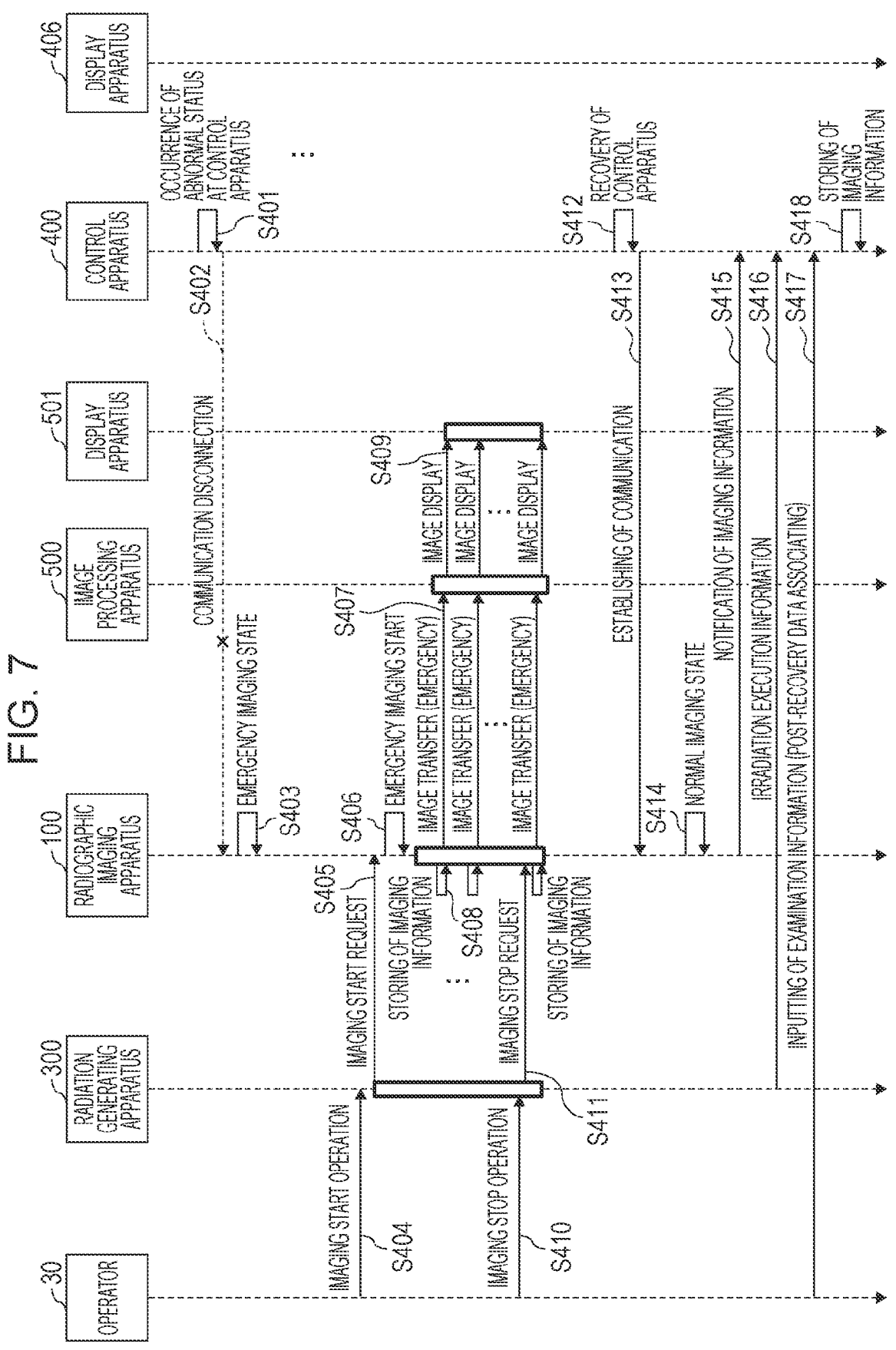
FIG. 7 is a sequence chart that illustrates an example of processing steps in an emergency imaging state of the radiographic imaging system according to the first embodiment of the present disclosure.

FIG. 7 is a sequence chart that illustrates an example of processing steps in an emergency imaging state of the radiographic imaging system 10 according to the first embodiment of the present disclosure. In FIG. 7, the same reference numerals are assigned to components that are the same as those illustrated in FIGS. 1 and 6, and a detailed explanation thereof will be omitted.

In step S401, some kind of abnormal status occurs at the control apparatus 400. Next, in step S402, a communication between the radiographic imaging apparatus 100 and the control apparatus 400 is disconnected.

Next, upon the disconnection of the communication with the control apparatus 400, in step S403, the radiographic imaging apparatus 100 is shifted into an emergency imaging state by imaging state determination. In this case, the radiographic imaging apparatus 100 is unable to receive instructions on image acquisition conditions such as image size, frame rate, sensitivity, etc. from the control apparatus 400. Therefore, an automatic change to specific image acquisition conditions having been set in advance is executed.

Next, in step S404, the operator 30 performs an operation for starting imaging by using the operation UI 302 of the radiation generating apparatus 300 when performing radiographic imaging.

Next, in step S405, a signal for an imaging start request is transmitted from the radiation generating apparatus 300 to the radiographic imaging apparatus 100.

Next, in step S406, upon receiving the imaging start request, the radiographic imaging apparatus 100 starts emergency imaging operation corresponding to the image acquisition conditions set for the emergency imaging state.

Next, in step S407, the radiographic imaging apparatus 100 transfers, to the image processing apparatus 500, a radiographic image acquired in accordance with the radiation rays R applied from the radiation generating apparatus 300. When performing the image transfer in step S407, together with sending the radiographic image, the radiographic imaging apparatus 100 notifies the image processing apparatus 500 to the effect that said image that is being transferred is the radiographic image acquired when in the emergency imaging state. This notification may be performed in the form of accompanying information of the radiographic image such as an image header or may be performed by any other means such as command notification prior to the transfer of the radiographic image. The radiographic imaging apparatus 100, when in the emergency imaging state, is unable to communicate with the control apparatus 400 and is therefore unable to transmit radiographic imaging information to the control apparatus 400 for storage thereat.

For this reason, in step S408, the radiographic imaging apparatus 100 stores the radiographic imaging information in the radiographic imaging into the first storage unit 140 as the radiographic imaging information 141.

Next, in step S409, based on the notification from the radiographic imaging apparatus 100, the image processing apparatus 500 recognizes that the received image is the radiographic image acquired when in the emergency imaging state. Then, the image processing apparatus 500 causes the display apparatus 501, which is connected to the image processing apparatus 500 and is provided for use in an emergency imaging state, to display the radiographic image directly, instead of transferring the radiographic image to the control apparatus 400.

In a case of moving-picture imaging, the processing from the image transfer in step S407 to the image display in step S409 is executed repeatedly.

After that, when stopping the radiographic imaging, in step S410, the operator 30 performs an operation for stopping the imaging by using the operation UI 302 of the radiation generating apparatus 300.

Next, in step S411, a signal for an imaging stop request is transmitted from the radiation generating apparatus 300 to the radiographic imaging apparatus 100. Upon receiving the imaging stop request, the radiographic imaging apparatus 100 stops the radiographic imaging operation. Through this step, the radiographic imaging information in the radiographic imaging executed when in the emergency imaging state is stored into the first storage unit 140 of the radiographic imaging apparatus 100.

After that, in step S412, the control apparatus 400 recovers. Next, in step S413, a communication between the radiographic imaging apparatus 100 and the control apparatus 400 is established normally.

Next, in step S414, the radiographic imaging apparatus 100 is shifted into a normal imaging state by imaging state determination.

Next, in step S415, the radiographic imaging apparatus 100 transmits the radiographic imaging information 141 that was stored in the first storage unit 140 under the emergency imaging state to the control apparatus 400.

Next, in step S416, the control apparatus 400 acquires the irradiation execution information pertaining to the execution when in the emergency imaging state from the radiation generating apparatus 300.

After that, in step S417, the operator 30 inputs the examination information pertaining to the execution when in the emergency imaging state into the control apparatus 400 as needed.

Next, in step S418, the control apparatus 400 stores the radiographic imaging information acquired in step S415, the irradiation execution information acquired in step S416, and the examination information acquired in step S417 in association with one another as the radiographic imaging information pertaining to the execution when in the emergency imaging state.

In the present embodiment, the image processing apparatus 500 is configured as a discrete apparatus that is independent of the radiographic imaging apparatus 100; however, for example, it may be configured as one of functions of the radiographic imaging apparatus 100. In this case, the display apparatus 501 may be configured to be directly connectable to the radiographic imaging apparatus 100.

As explained above, the radiographic imaging apparatus 100 according to the first embodiment is configured to be able to communicate with the control apparatus 400 and includes the radiation detecting unit 101 configured to detect incident radiation rays R to acquire a radiographic image. The radiographic imaging apparatus 100 according to the first embodiment further includes a storage unit 140, 150 configured to, in a case where radiographic imaging is performed when in an emergency imaging state (a first imaging state), in which a state of communication with the control apparatus 400 is not normal, store radiographic imaging information in the radiographic imaging. The radiographic imaging apparatus 100 according to the first embodiment further includes a communication control unit 160 configured to, upon a transition from the emergency imaging state to a normal imaging state (a second imaging state), in which the state of communication with the control apparatus 400 is normal, transmit the radiographic imaging information stored in the storage unit to the control apparatus 400.

With this configuration, it is possible to grasp what kind of radiographic imaging was executed in a case of execution of the radiographic imaging at the radiographic imaging apparatus 100 while the state of communication with the control apparatus 400 was not normal.

Second Embodiment

Next, a second embodiment of the present disclosure will now be described. In the description of the second embodiment below, an explanation will be omitted for matters that are the same as those in the first embodiment described above, and matters that are different from those in the first embodiment described above will be mainly described.

Figure 8:
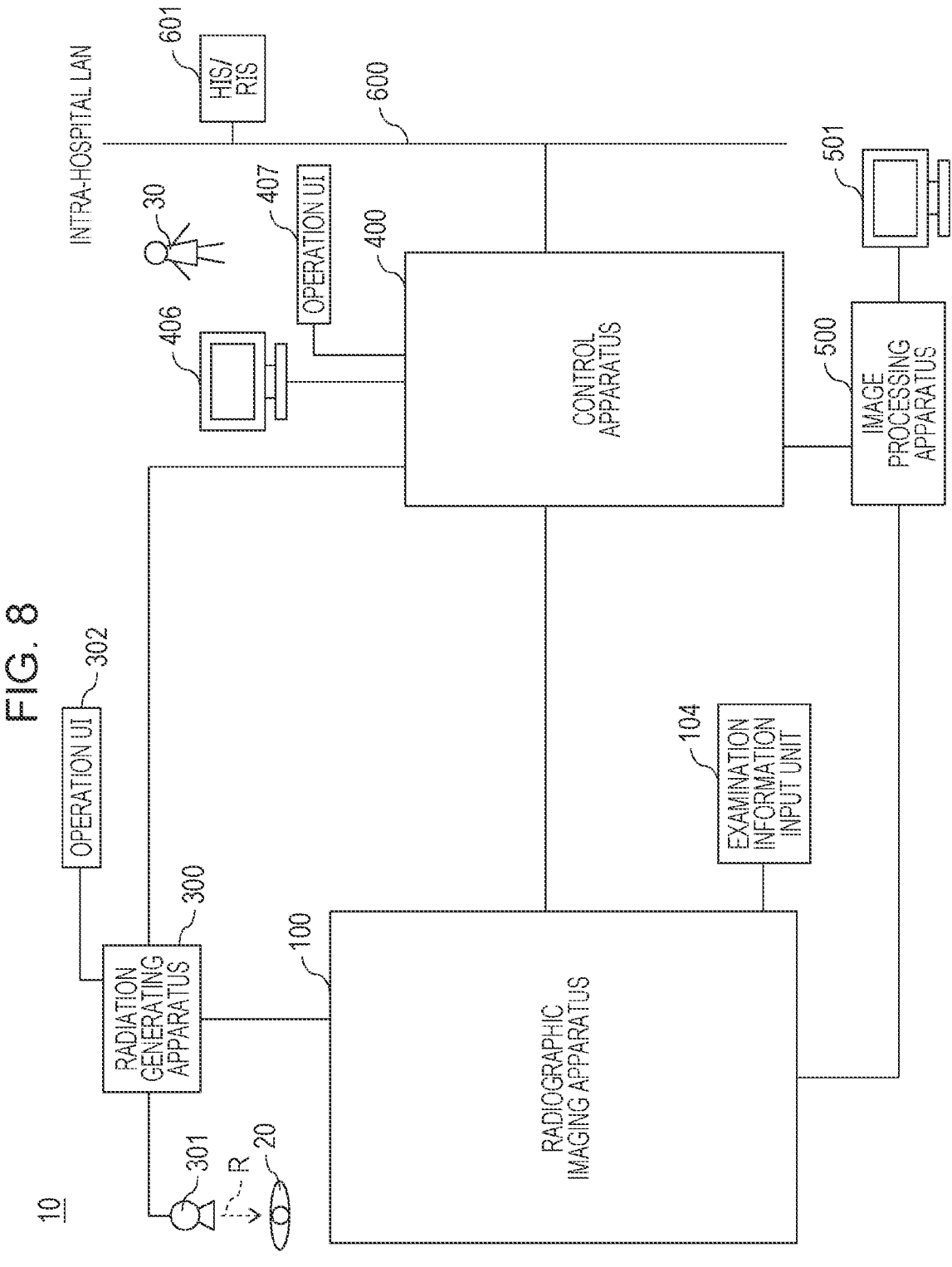
FIG. 8 is a diagram that illustrates an example of a schematic configuration of a radiographic imaging system according to a second embodiment of the present disclosure.

FIG. 8 is a diagram that illustrates an example of a schematic configuration of a radiographic imaging system 10 according to a second embodiment of the present disclosure. In FIG. 8, the same reference numerals are assigned to components that are the same as those illustrated in FIG. 1, and a detailed explanation thereof will be omitted.

Specifically, the radiographic imaging system 10 according to the second embodiment illustrated in FIG. 8 further includes an examination information input unit 104 in addition to the components of the radiographic imaging system 10 according to the first embodiment illustrated in FIG. 1. Although the internal configuration of the radiographic imaging apparatus 100 is not illustrated in FIG. 8, the radiographic imaging apparatus 100 according to the second embodiment also includes the components 101 to 103 that are the same as those of FIG. 1. Furthermore, although the internal configuration of the control apparatus 400 is not illustrated in FIG. 8, the control apparatus 400 according to the second embodiment also includes the components 401 to 405 that are the same as those of FIG. 1.

The examination information input unit 104 is configured to be connectable to the radiographic imaging apparatus 100 and input examination information such as a patient ID and imaging protocol information, etc. into the radiographic imaging apparatus 100. The examination information input unit 104 is, for example, a barcode reader and configured to acquire examination information by scanning a barcode containing the examination information. In the present embodiment, the examination information input unit 104 can be configured as a component included in the radiographic imaging apparatus 100. Moreover, the examination information inputted from the examination information input unit 104 can be the examination information included in the radiographic imaging information at the radiographic imaging apparatus 100.

In the present embodiment, communication between the radiation generating apparatus 300 and the radiographic imaging apparatus 100 is not limited to exchanging of sync signals such as notification of a start and an end of irradiation with the radiation rays R and notification of an irradiation-possible timing of the radiation rays R, etc. In the present embodiment, exchanging of information such as irradiation execution information and irradiation iris setting information, etc. is also possible via communication between the radiation generating apparatus 300 and the radiographic imaging apparatus 100. The communication between the radiation generating apparatus 300 and the radiographic imaging apparatus 100 can be executed by means of any one or more of cable-connected communication compliant with an RS232C standard, a USB standard, an Ethernet standard, a CAN standard, or the like, communication via a dedicated signal line, and wireless communication.

Moreover, in the present embodiment, the radiographic imaging apparatus 100 is able to acquire not only the image acquisition information but also the examination information and the irradiation execution information as the radiographic imaging information. In a case where radiographic imaging is performed when in an emergency imaging state, all of the above-mentioned kinds of information can be stored into the storage unit of the radiographic imaging apparatus 100 as the radiographic imaging information.

Figure 9:
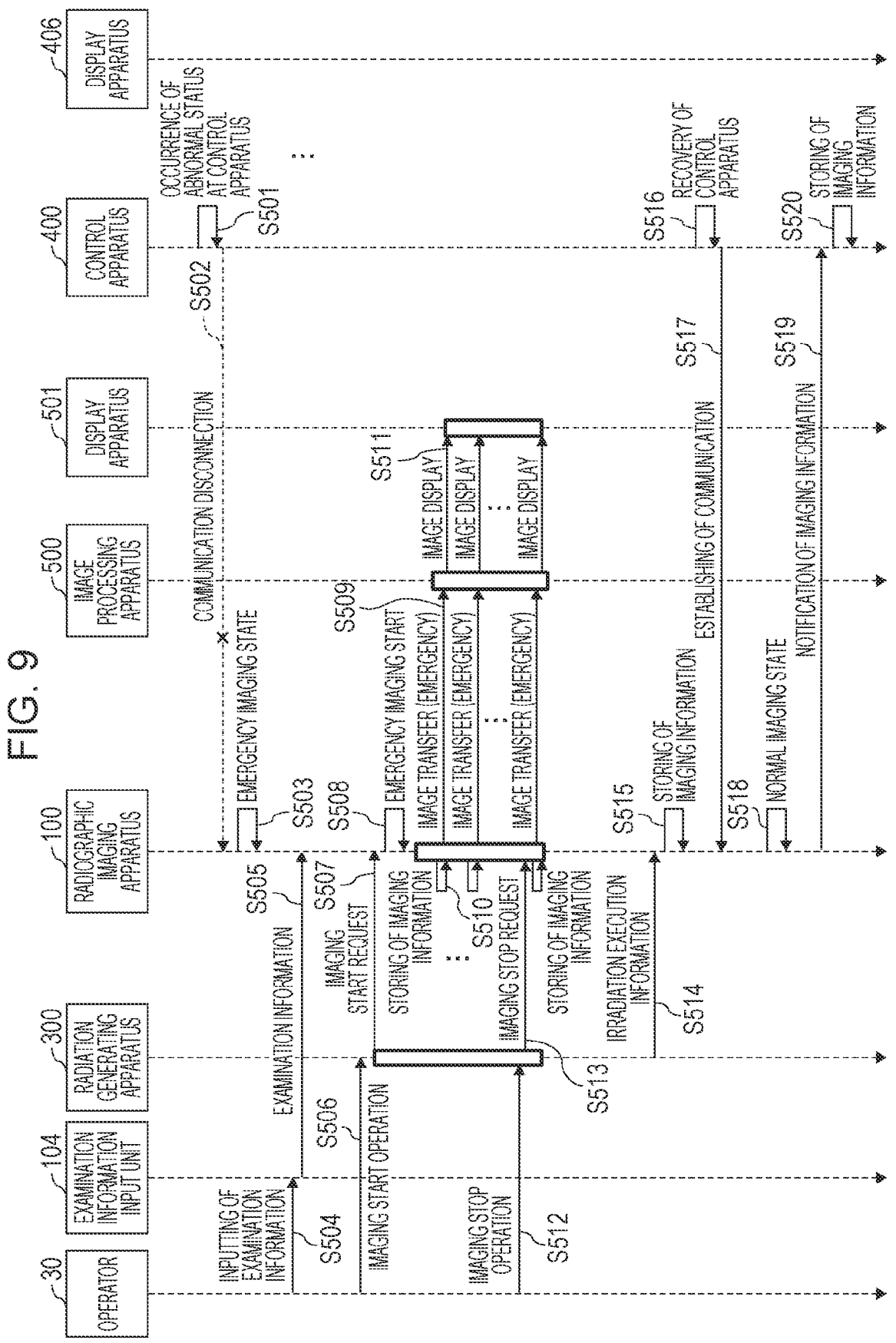
FIG. 9 is a sequence chart that illustrates an example of processing steps in an emergency imaging state of the radiographic imaging system according to the second embodiment of the present disclosure.

FIG. 9 is a sequence chart that illustrates an example of processing steps in an emergency imaging state of the radiographic imaging system 10 according to the second embodiment of the present disclosure. In FIG. 9, the same reference numerals are assigned to components that are the same as those illustrated in FIGS. 1, 6, and 8, and a detailed explanation thereof will be omitted.

In step S501, some kind of abnormal status occurs at the control apparatus 400. Next, in step S502, a communication between the radiographic imaging apparatus 100 and the control apparatus 400 is disconnected.

Next, upon the disconnection of the communication with the control apparatus 400, in step S503, the radiographic imaging apparatus 100 is shifted into an emergency imaging state by imaging state determination. In this case, the radiographic imaging apparatus 100 is unable to receive instructions on image acquisition conditions such as image size, frame rate, sensitivity, etc. from the control apparatus 400 and therefore starts to operate under specific image acquisition conditions having been set in advance.

Next, in step S504, the operator 30 inputs examination information to the examination information input unit 104.

Next, in step S505, the examination information input unit 104 inputs, to the radiographic imaging apparatus 100, the examination information having been inputted in step S504.

Next, in step S506, the operator 30 performs an operation for starting imaging by using the operation UI 302 of the radiation generating apparatus 300 when performing radiographic imaging.

Next, in step S507, a signal for an imaging start request is transmitted from the radiation generating apparatus 300 to the radiographic imaging apparatus 100. Next, in step S508, upon receiving the imaging start request, the radiographic imaging apparatus 100 starts emergency imaging operation corresponding to the image acquisition conditions set for the emergency imaging state.

Next, in step S509, the radiographic imaging apparatus 100 transfers, to the image processing apparatus 500, a radiographic image acquired in accordance with the radiation rays R applied from the radiation generating apparatus 300. When performing the image transfer in step S509, together with sending the radiographic image, the radiographic imaging apparatus 100 notifies the image processing apparatus 500 to the effect that said image that is being transferred is the radiographic image acquired when in the emergency imaging state. The radiographic imaging apparatus 100, when in the emergency imaging state, is unable to communicate with the control apparatus 400 and is therefore unable to transmit radiographic imaging information to the control apparatus 400 for storage thereat.

For this reason, in step S510, the radiographic imaging apparatus 100 stores the radiographic imaging information in the radiographic imaging into the first storage unit 140 as the radiographic imaging information 141.

Next, in step S511, based on the notification from the radiographic imaging apparatus 100, the image processing apparatus 500 recognizes that the received image is the radiographic image acquired when in the emergency imaging state. Then, the image processing apparatus 500 causes the display apparatus 501, which is connected to the image processing apparatus 500 and is provided for use in an emergency imaging state, to display the radiographic image directly, instead of transferring the radiographic image to the control apparatus 400.

In a case of moving-picture imaging, the processing from the image transfer in step S509 to the image display in step S511 is executed repeatedly.

After that, when stopping the radiographic imaging, in step S512, the operator 30 performs an operation for stopping the imaging by using the operation UI 302 of the radiation generating apparatus 300.

Next, in step S513, a signal for an imaging stop request is transmitted from the radiation generating apparatus 300 to the radiographic imaging apparatus 100. Upon receiving the imaging stop request, the radiographic imaging apparatus 100 stops the radiographic imaging operation. Through this step, the radiographic imaging information in the radiographic imaging executed when in the emergency imaging state is stored into the first storage unit 140 of the radiographic imaging apparatus 100.

Next, in step S514, the radiation generating apparatus 300 transmits, to the radiographic imaging apparatus 100, the irradiation execution information such as information about the irradiation conditions (tube voltage, tube current, irradiation time, and the like) of the radiation rays R in the executed moving-picture imaging and cumulative dose information and the like.

Next, in step S515, the radiographic imaging apparatus 100 stores the image acquisition information that includes the captured image that is the radiographic image having been captured, the examination information, and the irradiation execution information in association with one another into the first storage unit 140 as the radiographic imaging information.

Moreover, in the present embodiment, information that indicates the irradiation region of the radiation rays R can also be notified on a real-time basis from the radiation generating apparatus 300 to the radiographic imaging apparatus 100. Therefore, the radiographic imaging apparatus 100 is able to acquire cumulative pixel value information from the region of interest corresponding to the notified irradiation region as the image acquisition information.

After that, in step S516, the control apparatus 400 recovers. Next, in step S517, a communication between the radiographic imaging apparatus 100 and the control apparatus 400 is established normally.

Next, in step S518, the radiographic imaging apparatus 100 is shifted into a normal imaging state by imaging state determination.

Next, in step S519, the radiographic imaging apparatus 100 transmits the radiographic imaging information 141 that was stored in the first storage unit 140 under the emergency imaging state to the control apparatus 400.

Next, in step S520, the control apparatus 400 stores the radiographic imaging information acquired in step S519. In the present embodiment, the radiographic imaging information acquired in step S519 includes the examination information and the irradiation execution information, too; therefore, the control apparatus 400 is able to store the radiographic imaging information acquired in step S519 directly as is into the storage unit of the control apparatus 400.

The radiographic imaging apparatus 100 according to the second embodiment makes it possible to grasp what kind of radiographic imaging was executed in a case of execution of the radiographic imaging at the radiographic imaging apparatus 100 while the state of communication with the control apparatus 400 was not normal, similarly to the first embodiment.

Other Embodiments

The present disclosure may be embodied by supplying, to a system or an apparatus via a network or in the form of a storage medium, a program that realizes one or more functions of the embodiments described above, and by causing one or more processors in the system or the apparatus to read out and run the program. The disclosed concept can be embodied also by using one or more function-implementing circuits (e.g., ASIC).

The program, and a computer-readable storage medium storing the program, are also encompassed within the scope of the present disclosure.

The foregoing embodiments are just examples for implementation of the present disclosure, and, as such, shall not be construed to limit the technical scope of the present disclosure. That is, the present disclosure can be embodied in various ways without departing from its technical concept and its main features.

The disclosed technique makes it possible to grasp what kind of radiographic imaging was executed in a case of execution of the radiographic imaging at a radiographic imaging apparatus while the state of communication with a control apparatus was not normal.

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2022-178059, filed Nov. 7, 2022, which is hereby incorporated by reference herein in its entirety.

What is claimed is:

1. A radiographic imaging apparatus configured to communicate with a control apparatus, the radiographic imaging apparatus comprising:
a processor; and
a memory storing a program which, when executed by the processor causes the radiographic imaging apparatus to:
detect incident radiation rays to acquire a radiographic image;
determine whether the radiographic imaging apparatus is in a first imaging state, in which a state of communication with the control apparatus is not normal, or in a second imaging state, in which the state of communication is normal;
store radiographic imaging information in the first imaging state when it is determined that the radiographic imaging apparatus is in the first imaging state; and
transmit the radiographic imaging information to the control apparatus upon a transition from the first imaging state to the second imaging state.

2. The radiographic imaging apparatus according to claim 1, wherein
the radiographic imaging information includes at least one of examination information, image acquisition information, and irradiation execution information,
the examination information includes at least one of subject information in the radiographic imaging and imaging protocol information,
the image acquisition information includes at least one of a captured image that is the radiographic image acquired through the radiographic imaging, date-and-time information of the radiographic imaging, image acquisition conditions in acquiring the radiographic image, and cumulative pixel value information in a region of interest, and
the irradiation execution information includes at least one of irradiation condition information of the radiation rays and cumulative irradiation dose information of the radiation rays.

3. The radiographic imaging apparatus according to claim 2, wherein
the image acquisition information includes, as the captured image, the radiographic image of all frames acquired when in the first imaging state.

4. The radiographic imaging apparatus according to claim 2, wherein
the image acquisition information includes, as the captured image, a selected image selected from among the radiographic image of a plurality of frames acquired when in the first imaging state.

5. The radiographic imaging apparatus according to claim 4, wherein
the selected image is the radiographic image acquired last among the radiographic image of the plurality of frames.

6. The radiographic imaging apparatus according to claim 2, wherein
the image acquisition information includes, as the captured image, an image obtained by size-reducing or compressing the radiographic image acquired when in the first imaging state.

7. The radiographic imaging apparatus according to claim 2, wherein the processor further causes the radiographic imaging apparatus to:

input the examination information, wherein the radiographic imaging information includes the examination information inputted.

8. The radiographic imaging apparatus according to claim 2, wherein the processor further causes the radiographic imaging apparatus to:

acquire the irradiation execution information in irradiation with the radiation rays executed at a radiation generating apparatus configured to generate the radiation rays, wherein the radiographic imaging information includes the irradiation execution information.

9. The radiographic imaging apparatus according to claim 1, wherein when in the second imaging state, image acquisition conditions for acquiring the radiographic image are received from the control apparatus.

10. A method of controlling a radiographic imaging apparatus configured to be able to communicate with a control apparatus and including a radiation detecting unit configured to detect incident radiation rays to acquire a radiographic image, the method comprising:

determining whether the radiographic imaging apparatus is in a first imaging state, in which a state of communication with the control apparatus is not normal, or in a second imaging state, in which the state of communication is normal; and storing, in a case where it is determined that the radiographic imaging apparatus is in the first imaging state, radiographic imaging information in the first imaging state into a storage unit; and transmitting, upon a transition from the first imaging state to the second imaging state the radiographic imaging information stored in the storage unit to the control apparatus.

* * * * *